United States Patent [19]

Ackley

[11] Patent Number: 5,728,532
[45] Date of Patent: Mar. 17, 1998

[54] ELECTRODE CONFIGURATION FOR MATRIX ADDRESSING OF A MOLECULAR DETECTION DEVICE

[76] Inventor: Donald E. Ackley, 317 Goat Hill Rd., Lambertville, N.J. 08530

[21] Appl. No.: 655,797

[22] Filed: May 31, 1996

[51] Int. Cl.⁶ .......................... C12Q 1/68; C12P 19/34; G01N 33/53; G01N 15/06
[52] U.S. Cl. .................. 435/6; 435/5; 435/91.1; 435/91.5; 435/7.1; 435/7.9; 435/7.2; 435/292.1; 435/299.1; 435/808; 435/814; 536/24.3; 536/24.32; 536/24.33; 436/182; 436/501; 436/518; 436/524; 436/525; 436/528; 422/50; 422/81; 422/82; 422/68.1
[58] Field of Search .................. 435/6, 5, 91.2, 435/91.5, 91.1, 7.1–7.9, 292.1, 299.1, 808, 814; 536/24.3–24.33; 436/182, 501, 518, 524, 525, 528; 422/50, 81, 82, 68.1, 55, 56, 57, 58, 63, 69, 129, 131, 136; 530/322

[56] References Cited

U.S. PATENT DOCUMENTS 5,126,022  6/1992  Soane et al. ............... 204/180.1
5,527,670  6/1996  Stanley ............................ 435/6
5,532,128  7/1996  Eggers et al. ................ 436/116
5,605,662  2/1997  Heller et al. ................ 422/68.1

*Primary Examiner*—W. Gary Jones
*Assistant Examiner*—Dianne Rees

[57] ABSTRACT

An apparatus and method for selectively attracting and inhibiting attraction of at least one predetermined molecule to a site in a molecular detection device utilizes a first electrode and a second electrode proximate to the site. The first electrode selectively generates a first electric field proximate to the site in response to a first signal applied thereto. The first electric field provides an attractive force to attract the at least one predetermined molecule toward the site. The second electrode selectively generates a second electric field proximate to the site in response to a second signal applied thereto. The second electric field selectively inhibits attraction of the at least one predetermined molecule toward the site by providing a repulsive force which dominates the attractive force provided by the first electrode.

35 Claims, 3 Drawing Sheets

ELECTRODE CONFIGURATION FOR MATRIX ADDRESSING OF A MOLECULAR DETECTION DEVICE

FIELD OF THE INVENTION

The present invention relates to methods and systems for addressing binding sites in a molecular detection chip.

BACKGROUND OF THE INVENTION

Recently, an increased effort has been directed toward the development of chips for molecular detection. In general, a molecular detection chip includes a substrate on which an array of binding sites is arranged. Each binding site, or hybridization site, has a respective molecular receptor which hybridizes or binds with a molecule containing a predetermined structure. A sample solution is applied to the molecular detection chip, and molecules in the sample hybridize at one or more of the binding sites. The particular binding sites at which hybridization occurs are detected, and one or more molecular structures within the sample are subsequently deduced.

Of great interest are molecular detection chips for gene sequencing. These chips, often referred to as DNA chips, utilize an array of selective binding sites each having respective single-stranded DNA probes. A sample of single-stranded DNA fragments, referred to as target DNA, is applied to the DNA chip. The DNA fragments attach to one or more of the DNA probes by a hybridization process. By detecting which DNA probes have a DNA fragment hybridized thereto, a sequence of nucleotide bases within the DNA fragment can be determined.

To hasten the hybridization process, a local concentration of target DNA can be increased at predetermined sites using electric field enhancements. Here, each site has an electrode associated therewith for selectively generating an electric field thereby. The electric field is generated by applying an electric potential difference between an electrode at the site and a counter electrode at a peripheral portion of the chip. To attract DNA fragments to the site, the polarity of the electric potential difference is selected to generate an electric field having a polarity opposite to the charge of the DNA fragments. To dehybridize the site, an electric field having the same polarity as the DNA fragments can be generated to repel the DNA fragments from the site.

For applications such as self-addressing and self-assembling of molecular detection chips, it is beneficial that the hybridization and de-hybridization of the sites be individually controllable. PCT Publication Number WO 95/12808 to Nanogen, Inc. discloses a molecular detection device which maintains an individual controllability of each site using the above-described electrode configuration. This individual controllability is provided by connective circuitry for each individual electrode to an outside perimeter of contact pads. Such a configuration of contact pads is illustrated for addressing electrodes at sixty-four sites. However, for molecular detection chips having substantially more than sixty-four sites, the number of individual contact pads for addressing the electrodes becomes impractical.

BRIEF DESCRIPTION OF THE DRAWINGS

The invention is pointed out with particularity in the appended claims. However, other features of the invention will become more apparent and the invention will be best understood by referring to the following detailed description in conjunction with the accompanying drawings in which:

DETAILED DESCRIPTION OF A PREFERRED EMBODIMENT

Embodiments of the present invention advantageously provide electrode configurations for a molecular detection device which allows for matrix addressing of the sites. In comparison to having an individual contact for each site, this approach significantly reduces the number of externally-accessible contacts required. Embodiments of the present invention allow single sites of the molecular detection device to be individually addressed in a controlled manner. If desired, a plurality of sites in the molecular detection device can be addressed simultaneously.

Figure 1:
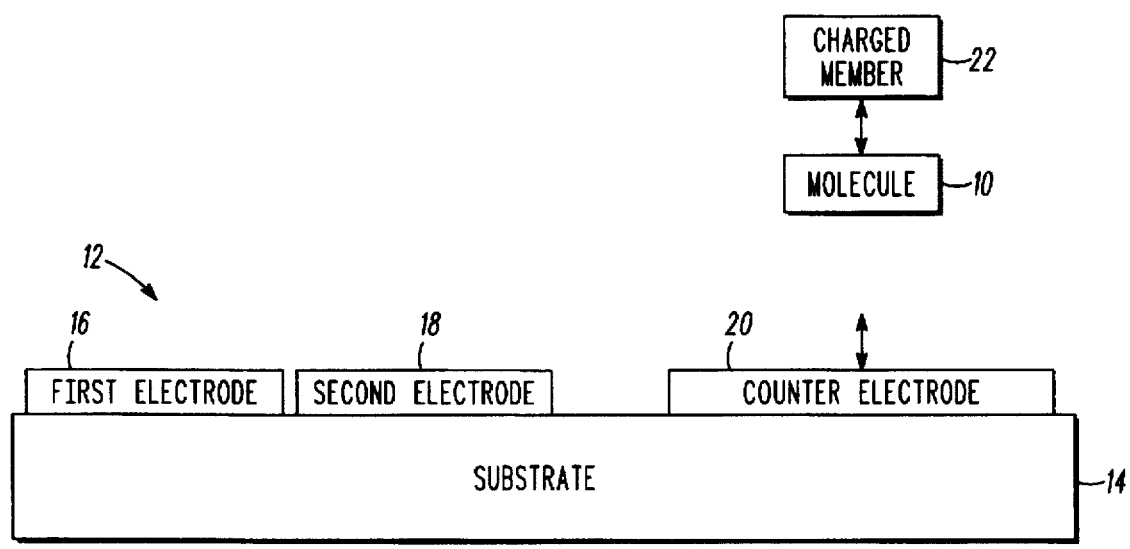
FIG. 1 is a block diagram of an embodiment of an apparatus for selectively attracting and inhibiting attraction of at least one predetermined molecule to a site in a molecular detection device.

FIG. 1 is a block diagram of an embodiment of an apparatus for selectively attracting and inhibiting attraction of at least one predetermined molecule 10 to a site 12 in a molecular detection device 14. The apparatus includes a first electrode 16 and a second electrode 18 proximate to the site 12.

The first electrode 16 selectively generates a first electric field proximate to the site 12 in response to a first signal applied thereto. The first electric field provides an attractive force to attract the at least one predetermined molecule 10 toward the site 12. To attract the at least one molecule 10 toward the site 12, the polarity of the first electric field is selected to have a polarity opposite to a charge associated with the at least one molecule 10. The first electric field can be generated by applying a suitable voltage between the first electrode 16 and a counter electrode 20 located away from the site 12.

The second electrode 18 selectively generates a second electric field proximate to the site 12 in response to a second signal applied thereto. The second electric field selectively inhibits attraction of the at least one predetermined molecule 10 toward the site 12 by providing a repulsive force which dominates the attractive force provided by the first electric field. The repulsive force acts to repel the at least one predetermined molecule 10 away from the site 12. To repel the at least one molecule 10 away from the site 12, the polarity of the second electric field is selected to have the same polarity as the charge associated with the at least one molecule 10. The second electric field can be generated by applying a suitable voltage between the second electrode 18 and the counter electrode 20.

As a result, the at least one predetermined molecule 10 is selectively attracted to and repelled from the site 12 based upon two signals: the first signal applied to the first electrode 16 and the second signal applied to the second electrode 18. The use of two signals per site provides a basis for matrix addressing of a plurality of sites in a molecular detection device. Methods and systems for matrix addressing, which are described hereinafter, eliminate the need for individual controlling connections for each site in a molecular detection device.

The charge associated with the at least one predetermined molecule 10 can be inherent in the molecule, such as the inherent charge in a nucleotide or a DNA molecule. The charge associated with the at least one predetermined molecule 10 may also result from a charged member 22 attached to the at least one predetermined molecule 10. For example, at least one charged bead can be attached to the at least one predetermined molecule 10 to provide a charge associated therewith. It is noted that the use of the charged member 22 is optional for the various embodiments of the present invention.

Based upon the signals applied to the first electrode 16 and the second electrode 18, the apparatus can be utilized to attract the at least one predetermined molecule 10 to the site 12 for performing hybridization and self-assembly steps, to screen the site 12 from receiving the at least one molecule, and to dehybridize the site 12 to remove the at least one molecule therefrom.

Figure 2:
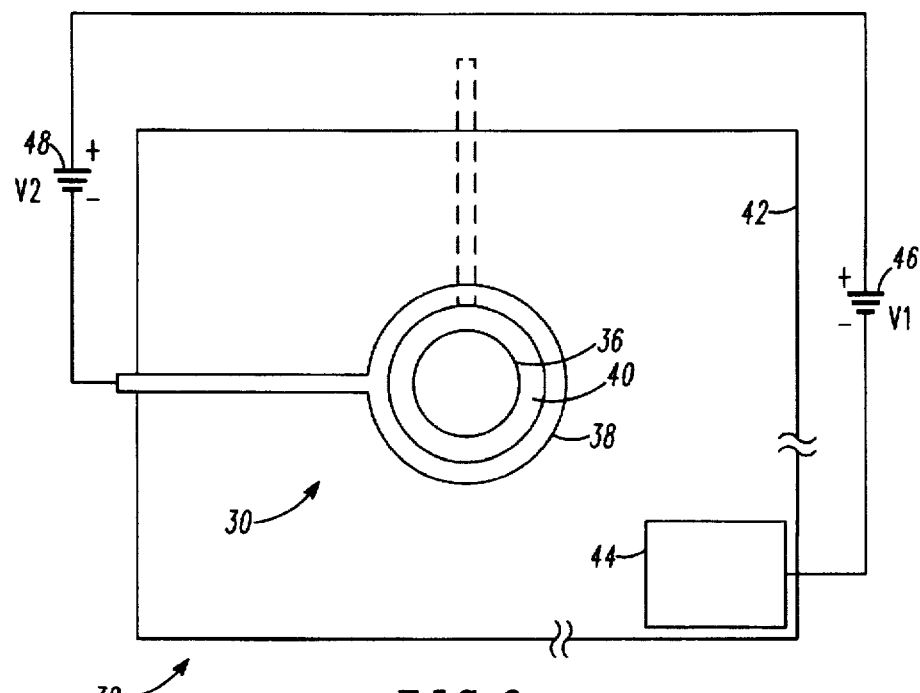
FIG. 2 is an illustration of an embodiment of an apparatus for selectively attracting and inhibiting attraction of molecules to a site in a molecular detection device.

FIG. 2 is an illustration of an embodiment of an apparatus for selectively attracting and inhibiting attraction of molecules to a site 30 in a molecular detection device 32. The apparatus includes a first electrode 36 and a second electrode 38 proximate to the site 30. The second electrode 38 defines an opening 40 which substantially surrounds an outer periphery of the first electrode 36. The second electrode 38 can, in general, surround only a portion of the outer periphery of the first electrode 36. In a preferred embodiment, however, the second electrode 38 is ring-shaped to fully surround the outer periphery of the first electrode 36 which is disk-shaped.

The first electrode 36 and the second electrode 38 are typically integrated with a substrate 42 of the molecular detection device 32. The first electrode 36 and the second electrode 38 can be disposed either on a common plane of the substrate 42, or on different planes. For example, the second electrode 38 can be non-coplanar to the first electrode 36 so that molecules must pass through the opening 40 to reach the first electrode 36.

To selectively attract or inhibit attraction to the site 30, the first electrode 36 and the second electrode 38 are selectively biased with respect to a counter electrode 44. The counter electrode 44 is disposed on the substrate 42 to contact a solution containing the molecules. Typically, the counter electrode 44 is disposed on a peripheral portion of the substrate 42, away from the site 30.

To attract predetermined molecules to the site 30, a DC voltage having a polarity opposite to the charge associated with the predetermined molecules is applied between the first electrode 36 and the counter electrode 44. For example, the first electrode 36 can be positively biased to attract negatively-charged molecules, such as molecules containing at least one nucleotide.

The second electrode 38 is utilized to inhibit the attraction of the molecules caused by the first electrode 36. To inhibit attraction of molecules to the site, a DC voltage having the same polarity as the charge associated with the molecules is applied between the second electrode 38 and the counter electrode 44. The magnitude of the DC voltage applied to the second electrode 38 is selected so that the repulsive force dominates the attractive force. For example, the second electrode 38 can be negatively biased to screen an attractive bias of the first electrode 36 to molecules containing at least one nucleotide.

The magnitudes of the DC voltages applied to the first electrode 36 and the second electrode 38 can be controlled to achieve a desired bias point on an electric field hybridization curve. This allows for improved control of hybridization in nucleic acid detection devices, such as DNA chips.

One approach to applying voltages to the first electrode 36 and the second electrode 38 is illustrated in FIG. 2. Here, a first voltage source 46 is connected between the first electrode 36 and the counter electrode 44. A second voltage source 48 is connected between the first electrode 36 and the second electrode 38. The voltage generated by the first voltage source is denoted by V1, and the voltage generated by the second voltage is denoted by V2.

To attract a molecule to the site 30, V1 is selected to be greater than V2. To selectively screen the site 30 from receiving a molecule, V2 is selected to be greater than V1. To dehybridize the site 30, the polarity of V1 is reversed. For DNA dehybridization, V1 and V2 are controlled to achieve a desired point on a DNA melting curve.

As an alternative to the above-described approach, the second voltage source 48 can be connected between the second electrode 38 and the counter electrode 44. The voltage, V2, applied to the second voltage source for attracting, screening, and repelling a molecule can be formulated accordingly.

Figure 3:
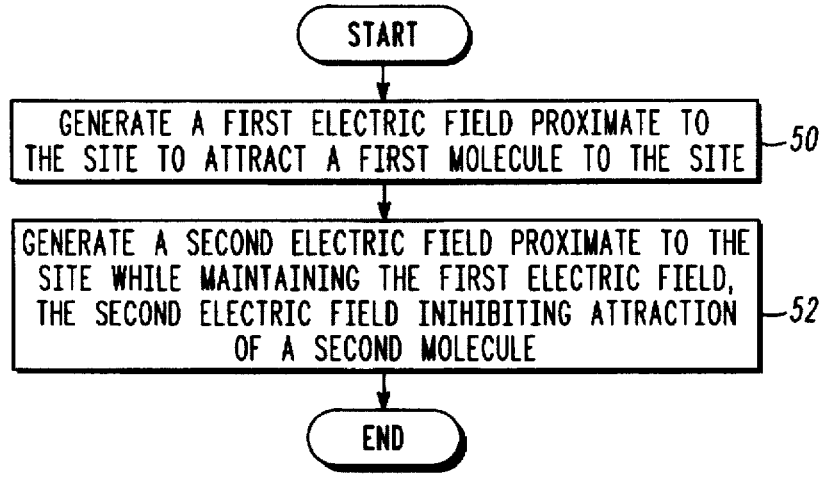
FIG. 3 shows a flow chart of a method of selectively attracting a first molecule to a site in a molecular detection device and selectively inhibiting attraction of a second molecule to the site.

FIG. 3 shows a flow chart of a method of selectively attracting a first molecule to a site in a molecular detection device and selectively inhibiting attraction of a second molecule to the site. Although the method is not limited to the specific molecules involved, of particular interest is a situation in which the first molecule and the second molecule each include at least one nucleotide, and where the site is a hybridization site in the molecular detection device.

As indicated by block 50, the method includes a step of generating a first electric field proximate to the site. The first electric field provides an attractive force to attract the first molecule toward the site. The step of generating the first electric field can include applying a first voltage between a first electrode proximate to the site and a counter electrode.

Upon generating the first electric field, the first molecule may bind to the hybridization site, as would occur if a molecular receptor for the first molecule is located at the hybridization site. Binding can also occur during self-assembly wherein a polymer chain is synthesized by sequentially coupling a series of molecules. Here, the first molecule is attracted to the site for placement at a predetermined location in the polymer chain.

As indicated by block 52, the method includes a step of generating a second electric field proximate to the site while maintaining the first electric field. The second electric field inhibits attraction of the second molecule toward the site by providing a repulsive force which dominates the attractive force provided by the first electric field. The repulsive force acts to repel the second molecule from the site.

The step of generating the second electric field can include applying a second voltage between a second electrode proximate to the site and the counter electrode. Here, the second voltage has a polarity opposite to the first voltage applied between the first electrode and the counter electrode, and has a magnitude greater than a magnitude of the first voltage.

The step of generating the second electric field can be performed after the first molecule binds to the hybridization site, in order to inhibit binding of the second molecule to the hybridization site. For example, binding or coupling can be inhibited during self-assembly if the second molecule is not desired at a particular location in the polymer chain.

Figure 4:
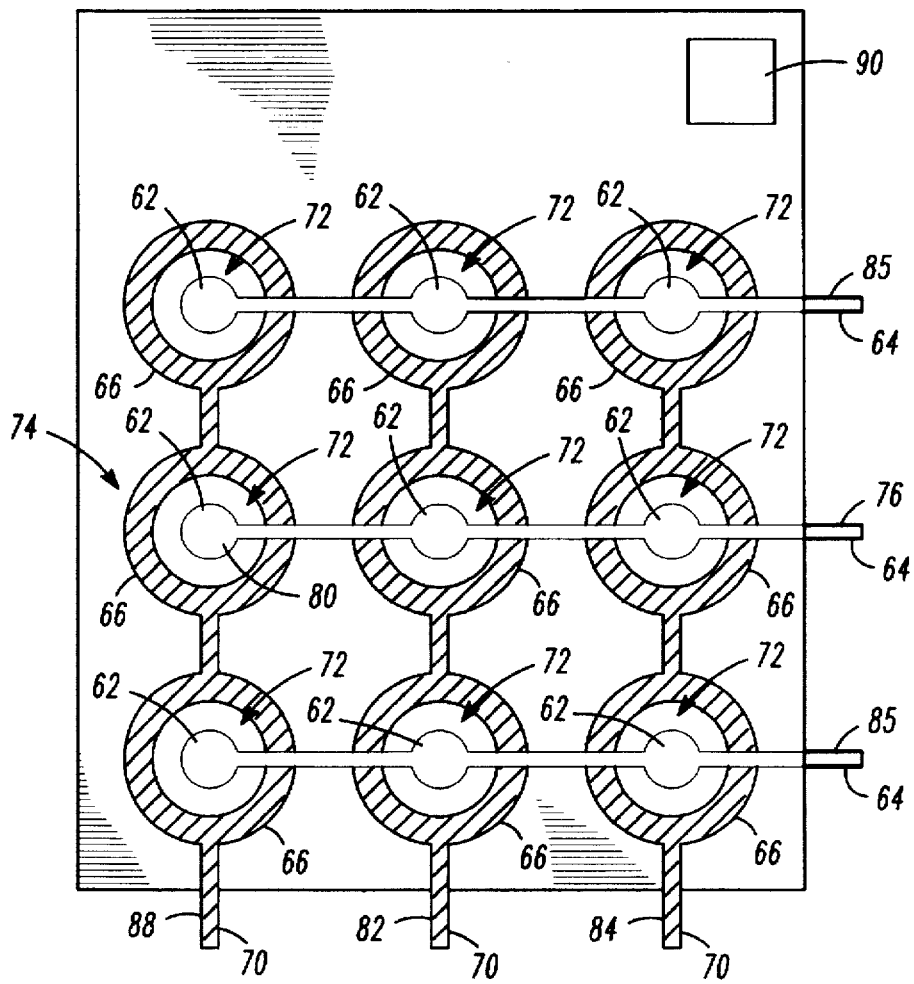
FIG. 4 is an illustration of an embodiment of an apparatus for individually addressing any of a plurality of binding sites for electric field enhancement in a molecular detection device.

FIG. 4 is an illustration of an embodiment of an apparatus for individually addressing any of a plurality of binding sites for electric field enhancement in a molecular detection device. The apparatus includes a first plurality of electrodes 62 arrayedly interconnected to form a first plurality of interconnected electrode arrays 64. In the illustrated embodiment, the first plurality of electrodes 62 are interconnected within each row of binding sites, but are unconnected between rows. Each of the first plurality of electrodes 62 is proximate to a respective one of the binding sites.

The apparatus further includes a second plurality of electrodes 66 arrayedly interconnected to form a second plurality of interconnected electrode arrays 70. In the illustrated embodiment, the second plurality of electrodes 66 are interconnected within each column of binding sites, but are unconnected between columns. Each of the second plurality of electrodes 66 is proximate to a respective one of the binding sites.

Each of the second plurality of electrodes 66 defines an opening 72 which surrounds at least a portion of the outer periphery of a respective one of the first plurality of electrodes 62. Preferably, each opening 72 completely surrounds the outer periphery of the respective one of the first plurality of electrodes 62. Here, each of the second plurality of electrodes 66 can be ring-shaped and each of the first plurality of electrodes 62 can be disk-shaped.

A predetermined binding site 74 is enhanced by applying an attractive potential to a first interconnected electrode array 76 having an electrode 80 proximate to the predetermined binding site 74. A repulsive potential is applied to at least one of the second plurality of interconnected electrode arrays 70 whose electrodes are distant from the predetermined binding site 74. These arrays are denoted by reference numerals 82 and 84. If desired, a repulsive potential can be applied to each of the second plurality of interconnected electrode arrays 70 whose electrodes are distant from the predetermined binding site 74 (i.e. the arrays denoted by reference numerals 82 and 84).

Arrays 85, of the first plurality of interconnected electrode arrays 64, whose electrodes are distant from the predetermined binding site 74 can receive a non-attractive potential so as not to attract molecules thereto.

To inhibit attraction to an electrode 86 proximate to the predetermined binding site 74, a slight repulsive potential is applied to an array 88 of the second plurality of interconnected arrays 70. The slight repulsive potential has a magnitude less than a magnitude of the attractive potential applied to the first interconnected electrode array 76.

The apparatus includes a counter electrode 90 which acts as a common reference for applying the attractive potential and repulsive potential to the interconnected electrode arrays. The counter electrode 90 is located distant from all of the plurality of binding sites.

Although illustrated by a 3×3 array of binding sites, it is noted that the above-described teachings can be applied to an array of any size.

Figure 5:
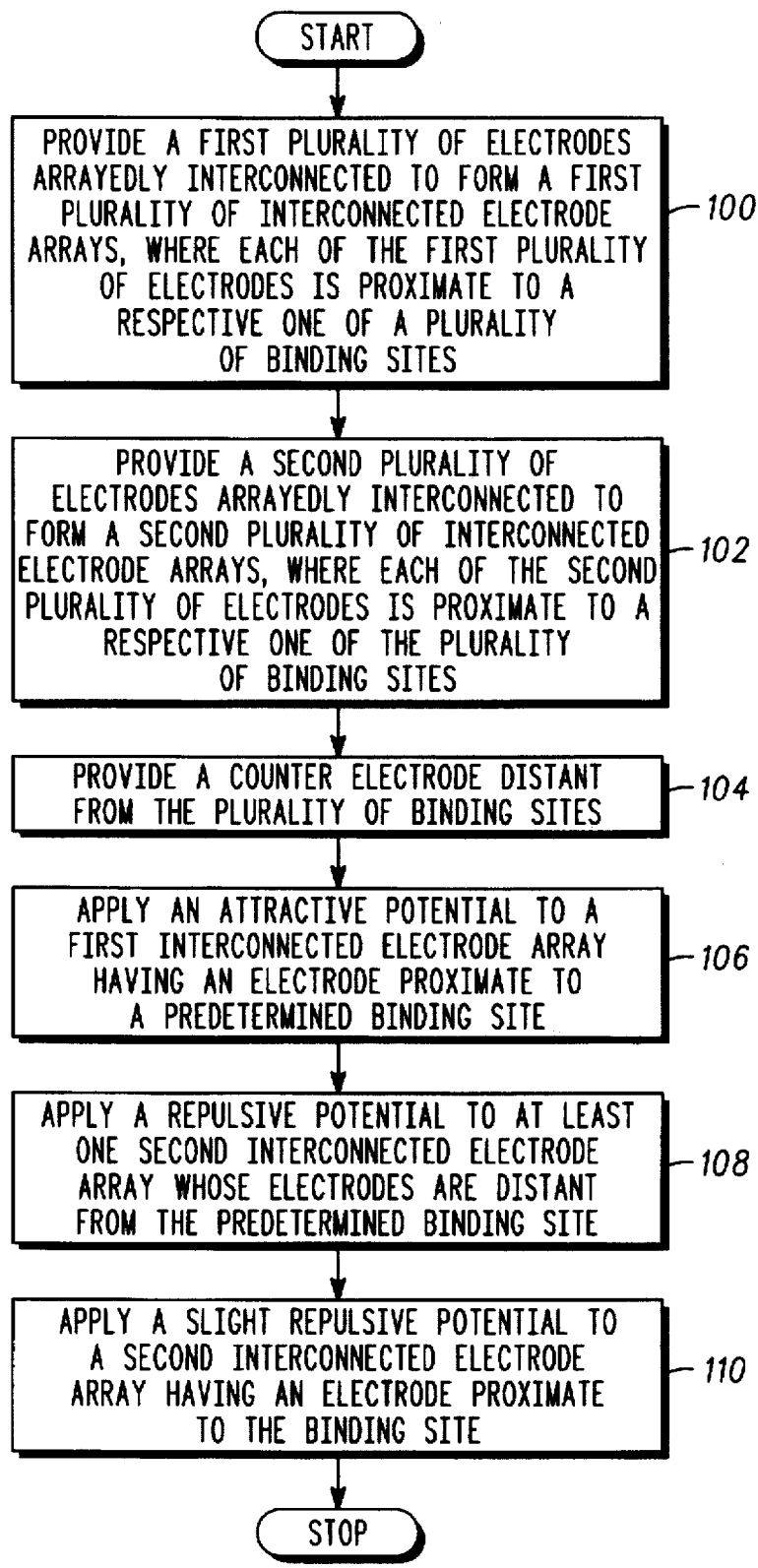
FIG. 5 is a flow chart of an embodiment of a method of individually addressing a predetermined binding site of a plurality of binding sites for electric field enhancement in a molecular detection device.

FIG. 5 is a flow chart of an embodiment of a method of individually addressing a predetermined binding site of a plurality of binding sites for electric field enhancement in a molecular detection device. The predetermined binding site can be an only one of the plurality of binding sites which is enhanced, or can be one of a plurality of the plurality of binding sites which is simultaneously enhanced.

As indicated by block 100, the method includes a step of providing a first plurality of electrodes arrayedly interconnected to form a first plurality of interconnected electrode arrays, where each of the first plurality of electrodes is proximate to a respective one of the plurality of binding sites. As indicated by block 102, the method further includes a step of providing a second plurality of electrodes arrayedly interconnected to form a second plurality of interconnected electrode arrays, where each of the second plurality of electrodes is proximate to a respective one of the plurality of binding sites. As indicated by block 104, a step of providing a counter electrode, distant from the plurality of binding sites, can also be performed. The steps indicated by blocks 100, 102, and 104 can be performed by providing an apparatus in accordance with the description of FIG. 4, although alternative embodiments of the method are not limited thereto.

As indicated by block 106, a step of applying an attractive potential to a first interconnected electrode array of the first plurality of interconnected electrode arrays is performed. The first interconnected electrode array includes an electrode proximate to a predetermined binding site of the plurality of binding sites. The attractive potential can be applied between the first interconnected electrode array and the counter electrode.

As indicated by block 108, a step of applying a repulsive potential to at least one of the second plurality of interconnected electrode arrays whose electrodes are distant from the predetermined binding site is performed. The repulsive potential can be applied between the at least one of the second plurality of interconnected electrode arrays and the counter electrode. The step of applying the repulsive potential can include applying a repulsive potential to each of the second plurality of interconnected electrode arrays whose electrodes are distant from the predetermined hybridization site.

As indicated by block 110, the method can further include the step of applying a repulsive potential to one of the second plurality of interconnected electrode arrays having an electrode proximate to the predetermined binding site. The repulsive potential is selected to have a magnitude less than a magnitude of the attractive potential applied to the first interconnected electrode array. This step is beneficial in keeping the one of the second plurality of interconnected electrode arrays clean from molecules.

Thus, there has been described herein a concept, as well as several embodiments including preferred embodiments of an electrode configuration for matrix addressing of a molecular detection device.

Because the various embodiments of the present invention provide an electrode configuration which allows for matrix addressing of the binding sites, they provide a significant improvement in reducing a number of externally-accessible contacts which are required for addressing individual sites. Embodiments of the present invention are well-suited for use in molecular detection chips which include, but are not limited to, DNA chips, RNA chips, immunosensors, and other biosensors.

It will be apparent to those skilled in the art that the disclosed invention may be modified in numerous ways and may assume many embodiments other than the preferred form specifically set out and described above.

Accordingly, it is intended by the appended claims to cover all modifications of the invention which fall within the true spirit and scope of the invention.

What is claimed is:

1. An apparatus for selectively attracting and inhibiting attraction of at least one molecule to a site in a molecular detection device, the apparatus comprising:
   a first electrode which selectively generates a first electric field in response to a first signal applied thereto, the first electric field providing an attractive force to attract the at least one molecule toward the site; and
   a second electrode which selectively generates a second electric field in response to a second signal applied thereto, the second electric field selectively inhibiting attraction of the at least one molecule toward the site by providing a repulsive force which dominates the attractive force provided by the first electric field, wherein the repulsive force repels the at least one molecule away from the site, and wherein the second electrode defines an opening that surrounds at least a portion of an outer periphery of the first electrode.

2. The apparatus of claim 1 wherein the at least one predetermined molecule includes at least one nucleotide, and wherein the site is a hybridization site in the molecular detection device.

3. The apparatus of claim 1 wherein the second electrode defines an opening which surrounds the outer periphery of the first electrode.

4. The apparatus of claim 3 wherein the second electrode is ring-shaped, and wherein the first electrode is disk-shaped.

5. The apparatus of claim 1 further comprising a counter electrode, wherein the first electric field is generated by applying a first voltage between the first electrode and the counter electrode, and wherein the second electric field is generated by applying a second voltage between the second electrode and the counter electrode.

6. A method of selectively attracting a first molecule to a site in a molecular detection device and selectively inhibiting attraction of a second molecule to the site, the method comprising the steps of:
   generating a first electric field, the first electric field providing an attractive force to attract the first molecule toward the site; and
   generating a second electric field while maintaining the first electric field, the second electric field inhibiting attraction of the second molecule toward the site by providing a repulsive force which dominates the attractive force provided by the first electric field, wherein the repulsive force repels the second molecule from the site.

7. The method of claim 6 wherein the first molecule and the second molecule each include at least one nucleotide, and wherein the site is a hybridization site in the molecular detection device.

8. The method of claim 7 wherein the first molecule binds to the hybridization site.

9. The method of claim 8 wherein the step of generating the second electric field is performed after the first molecule binds to the hybridization site, and wherein the step of generating the second electric field inhibits binding of the second molecule to the hybridization site.

10. The method of claim 6 wherein the step of generating the first electric field includes applying a first voltage between a first electrode proximate to the site and a counter electrode, and wherein the step of generating the second electric field includes applying a second voltage between a second electrode proximate to the site and the counter electrode.

11. The method of claim 10 wherein the second voltage has a magnitude greater than the first voltage and a polarity opposite to the first voltage.

12. The method of claim 10 wherein the second electrode defines an opening which surrounds at least a portion of an outer periphery of the first electrode.

13. The method of claim 12 wherein the second electrode is ring-shaped, and wherein the first electrode is disk-shaped.

14. An apparatus for individually addressing any of a plurality of binding sites for electric field enhancement in a molecular detection device, the apparatus comprising:
   a first plurality of electrodes interconnected to form a first plurality of interconnected electrode arrays, each of the first plurality of electrodes positioned to apply a field to a respective one of the plurality of binding sites; and
   a second plurality of electrodes interconnected to form a second plurality of interconnected electrode arrays, each of the second plurality of electrodes positioned to apply a field to a respective one of the plurality of binding sites;
   wherein at least one of the second plurality of electrodes defines an opening which surrounds at least a portion of an outer periphery of a respective one of the first plurality of electrodes.

15. The apparatus of claim 14 wherein each opening substantially surrounds the outer periphery of the respective one of the first plurality of electrodes.

16. The apparatus of claim 15 wherein each of the second plurality of electrodes is ring-shaped, and wherein each of the first plurality of electrodes is disk-shaped.

17. The apparatus of claim 14 wherein a first potential is applied to at least one of the first plurality of interconnected electrode arrays and a second potential is applied to at least one of the second plurality of interconnected electrode arrays.

18. The apparatus of claim 17 wherein a potential is applied to a group of the second plurality of interconnected electrode arrays.

19. The apparatus of claim 17 wherein the first potential is an attractive potential and the second potential is a repulsive potential.

20. The apparatus of claim 19 wherein the repulsive potential has a magnitude less than a magnitude of the attractive potential applied to the first interconnected electrode array.

21. The apparatus of claim 17 further comprising a counter electrode, wherein the second potential is applied between the at least one of the second plurality of interconnected electrode arrays and the counter electrode.

22. The apparatus of claim 17 wherein the first potential is an attractive potential.

23. The apparatus of claim 17 further comprising a counter electrode wherein the first potential is applied between at least one of the first plurality of electrodes and the counter electrode.

24. A method of individually addressing at least one of a plurality of binding sites for electric field enhancement in a molecular detection device, the method comprising the steps of:
   providing a first plurality of electrodes interconnected to form a first plurality of interconnected electrode arrays, each of the first plurality of electrodes positioned to apply a field to a respective one of the plurality of binding sites;
   providing a second plurality of electrodes interconnected to form a second plurality of interconnected electrode arrays, each of the second plurality of electrodes positioned to apply a field to a respective one of the plurality of binding sites;

applying an attractive potential to a first interconnected electrode array of the first plurality of interconnected electrode arrays, the first interconnected electrode array including a first electrode positioned to apply a field to at least one of the plurality of binding site; and applying a repulsive potential to at least one of the second plurality of interconnected electrode arrays, the at least one of the second plurality of interconnected electrode arrays disposed farther from the at least one of the plurality of binding sites than the first electrode thereby one of, attracting and repulsing a selected molecule to said at least one binding site.

25. The method of claim 24 wherein each of the second plurality of electrodes defines an opening which surrounds at least a portion of an outer periphery of a respective one of the first plurality of electrodes.

26. The method of claim 24 wherein each opening substantially surrounds the outer periphery of the respective one of the first plurality of electrodes.

27. The method of claim 24 wherein each of the second plurality of electrodes is ring-shaped, and wherein each of the first plurality of electrodes is disk-shaped.

28. The method of claim 24 wherein the step of applying the repulsive potential includes applying a repulsive potential to each of the second plurality of interconnected electrode arrays.

29. The method of claim 24 wherein the repulsive potential has a magnitude less than a magnitude of the attractive potential applied to the first interconnected electrode array.

30. The method of claim 24 further comprising the step of providing a counter electrode, wherein the attractive potential is applied between the first interconnected electrode array and the counter electrode, and wherein the repulsive potential is applied between the at least one of the second plurality of interconnected electrode arrays and the counter electrode.

31. An apparatus for applying a field to a molecule at a site in a molecular detection device, the apparatus comprising:

a first electrode which generates a first electric field in response to a first signal applied thereto, the first electric field applied to the molecule; and a second electrode which generates a second electric field in response to a second signal applied thereto, the second electric field applied to the molecule, the second electrode having an opening that surrounds at least a portion of an outer periphery of the first electrode.

32. The apparatus of claim 31 wherein the molecule comprises at least one nucleotide, and wherein the site is a hybridization site in the molecular detection device.

33. The apparatus of claim 34 wherein the second electrode defines an opening which surrounds the outer periphery of the first electrode.

34. The apparatus of claim 31 wherein the second electrode is ring-shaped, and wherein the first electrode is disk-shaped.

35. The apparatus of claim 31 further comprising a counter electrode, wherein the first electric field is generated by applying a first voltage between the first electrode and the counter electrode, and wherein the second electric field is generated by applying a second voltage between the second electrode and the counter electrode.

* * * * *

UNITED STATES PATENT AND TRADEMARK OFFICE
CERTIFICATE OF CORRECTION

PATENT NO. : 5,728,532
DATED : March 17, 1998
INVENTOR(S) : Ackley, Donald

It is certified that error appears in the above-indentified patent and that said Letters Patent is hereby corrected as shown below:

In Claim 33, column 10, line19, please delete "34" and add "31".

Signed and Sealed this

Twenty-second Day of June, 1999

Attest:

Q. TODD DICKINSON

Attesting Officer

Acting Commissioner of Patents and Trademarks